(12) United States Patent
Jiang et al.

(10) Patent No.: US 11,730,392 B2
(45) Date of Patent: Aug. 22, 2023

(54) BREATHING-DRIVEN FLEXIBLE RESPIRATORY SENSOR AND PREPARATION METHOD THEREOF

(71) Applicant: University of Electronic Science and Technology of China, Sichuan (CN)

(72) Inventors: Yadong Jiang, Sichuan (CN); Huiling Tai, Sichuan (CN); Bohao Liu, Sichuan (CN); Si Wang, Sichuan (CN); Zhen Yuan, Sichuan (CN); Qi Huang, Sichuan (CN); Guangzhong Xie, Sichuan (CN)

(73) Assignee: University of Electronic Science and Technology of China, Sichuan (CN)

( * ) Notice: Subject to any disclaimer, the term of this patent is extended or adjusted under 35 U.S.C. 154(b) by 1044 days.

(21) Appl. No.: 16/538,826

(22) Filed: Aug. 13, 2019

(65) Prior Publication Data
US 2019/0357807 A1    Nov. 28, 2019

(30) Foreign Application Priority Data
Aug. 30, 2018    (CN) .......................... 201811000346.6

(51) Int. Cl.
*A61B 5/08*     (2006.01)
*A61B 5/09*     (2006.01)
(Continued)

(52) U.S. Cl.
CPC .............. *A61B 5/083* (2013.01); *A61B 5/087* (2013.01); *A61B 5/0816* (2013.01); *A61B 5/093* (2013.01);
(Continued)

(58) Field of Classification Search
CPC ....... A61B 5/083; A61B 5/0816; A61B 5/087; A61B 5/093; A61B 5/113; A61B 5/4836; A61M 16/024; A61M 2016/0021
See application file for complete search history.

(56) References Cited

U.S. PATENT DOCUMENTS

| 2013/0213140 A1* | 8/2013 | Eichhorn .............. G01L 1/2206 977/956 |
| 2014/0288454 A1* | 9/2014 | Paz ....................... A61B 5/4845 600/532 |
| 2017/0119280 A1* | 5/2017 | Ahmad .................. A61B 5/097 |

FOREIGN PATENT DOCUMENTS

| CN | 105871247 A * | 8/2016 | ............. H01G 11/48 |
| CN | 106989767 A * | 7/2017 | ............. G01D 18/00 |

OTHER PUBLICATIONS

Wen, Z., Shen, Q. & Sun, X. Nanogenerators for Self-Powered Gas Sensing. Nano-Micro Lett. 9, 45 (2017). https://doi.org/10.1007/s40820-017-0146-4 (Year: 2017).*

* cited by examiner

*Primary Examiner* — Alex M Valvis
*Assistant Examiner* — Grace L Rozanski (57) ABSTRACT

A breathing-driven flexible respiratory sensor includes: a test cavity and a digital electrometer, wherein an upper internal wall of the test cavity is provided with an upper detecting component, and a lower internal wall of the test cavity is provided with a lower detecting component; the upper detecting component and the lower detecting component is arranged in a longitudinal symmetry form; wherein the upper detecting component comprises a substrate, an electrode and a gas sensitive film bonded in sequence from top to bottom, and the substrate is bonded to the upper internal wall of the test cavity; wherein a rubber airbag is disposed in the test cavity, and a friction film is bonded to
(Continued)

the rubber airbag; an air inlet cylinder is connected to a left end of the rubber airbag, and an air outlet cylinder is connected to a right end of the rubber airbag.

11 Claims, 4 Drawing Sheets

(51) Int. Cl.
    *G01N 27/00*     (2006.01)
    *A61B 5/083*     (2006.01)
    *A61B 5/087*     (2006.01)
    *A61M 16/00*     (2006.01)
    *A61B 5/093*     (2006.01)
    *A61B 5/113*     (2006.01)
    *A61B 5/00*     (2006.01)

(52) U.S. Cl.
    CPC ............. *A61B 5/113* (2013.01); *A61B 5/4836* (2013.01); *A61M 16/024* (2017.08); *A61M 2016/0021* (2013.01)

BREATHING-DRIVEN FLEXIBLE RESPIRATORY SENSOR AND PREPARATION METHOD THEREOF

CROSS REFERENCE OF RELATED APPLICATION

The present invention claims priority under 35 U.S.C. 119(a-d) to CN 201811000346.6, filed Aug. 30, 2018.

BACKGROUND OF THE PRESENT INVENTION

Field of Invention

The present invention relates to a technical field of microelectronics, and more particularly to a breathing-driven flexible respiratory sensor and a preparation method thereof.

Description of Related Arts

The composition of the human breath is complex. In addition to the main components of $N_2$, $O_2$, $CO_2$ and $H_2O$, there are hundreds of other trace gases. Changes in respiratory composition are derived from the metabolism of certain tissue structures within the body. Under normal circumstances, the concentration of these gases in the exhaled breath will be maintained within a certain range. However, if these tissue structures are diseased, their metabolism will be problematic, causing some intermediate products to be excreted with respiratory gas because they cannot be decomposed. Therefore, we can initially diagnose the disease of the human body by detecting the concentration of the target gas in the exhaled breath.

Conventionally, the methods for detecting exhaled breath mainly include gas chromatography, isotope calibration, and sensor detection. The principle of gas chromatography is to separate the gas by different flow rates in the stationary phase, and to detect the separated gas. Despite its high precision, the gas chromatograph is too bulky and expensive, which limits its application. Isotope calibration is commonly used for the detection of *Helicobacter pylori* infection: after oral administration of C-13 urea capsules, if *Helicobacter pylori* are present in the stomach, then the bacteria will decompose urease to hydrolyze urea. The hydrolyzed urea forms $CO_2$, which enters the lungs with blood and is discharged by gas. Then, the concentration of labeled C-13 in the gas exhaled by the patient is detected to determine the severity of the stomach disease. However, oral drugs have certain harm to the body, and the price of the detection device is relatively high. The sensor detection method is based on the reaction of the target gas with the metal or its oxide, resulting in a change in the electrical properties of the material. Such sensors have the advantages of low cost and low detection limit, but the sensor needs to be heated to provide the working conditions for testing, which seriously restricts its application in room temperature conditions. In recent years, the research on organic polymer gas sensitive materials is very hot. It has many advantages such as room temperature work, easy material availability, easy modification, low price, etc., and has gradually replaced metal oxides as the most promising new gas sensitive materials.

In recent decades, as fossil energy continues to he depleted and depleted, it is important to find a green, low-carbon, broad, and easily accessible source of energy. With the popularity of electronic products, the number of batteries used has increased dramatically. However, the recycling of harmful substances inside the conventional battery is bound to cause environmental pollution, and frequent replacement of the battery will also reduce the service life of the device. Therefore, if the working device itself can store energy or even self-generate to supply energy, a lot of manpower, material and financial resources will be saved. There are many micro-energy sources in nature, such as wind energy and tidal energy. However, due to the limitations of previous technologies and the low conversion efficiency, the exploration and utilization of such energy sources with broad application prospects has not been realized.

In 2012, the advent of a new type of energy-generating device, the friction nanogenerator, provided an opportunity for the use of micro-energy, which proved to be a device with extremely high conversion efficiency. Through the principle of combining frictional electrification and electrostatic induction, mechanical energy drives the device to periodically change the relative position, so that the induced charge of the device changes periodically, forming a reciprocating current in the external circuit. In combination with the application of the gas sensor, if the respiratory airflow is used as the driving source and the object to be tested, the friction nanogenerator and the organic polymer gas sensitive material are combined to form an integrated self-supply gas sensor, wherein there is no need for an additional energy supply system, the concentration of the target gas in the breathing gas is directly measured. Such sensors have broad application prospects.

SUMMARY OF THE PRESENT INVENTION

The present invention is directed to the problems that the conventional detection method is expensive, the practical temperature range is narrow, and the oral medicine required is harmful to the body. An object of the present invention is to provide a breathing-driven self-supply respiratory sensor with novel structure, low cost, high practicability and full utilization of natural energy. A rubber hag to which the friction material is attached undergoes expansion-contraction, causing contact-separation with the upper and lower gas sensitive films. Induced charges on the electrodes form a loop with the ground, thereby generating an alternating output.

Accordingly, in order to accomplish the above objects, the present invention provides:

a breathing-driven flexible respiratory sensor, comprising: a test cavity and a digital electrometer, wherein an upper internal wall of the test cavity is provided with an upper detecting component, and a lower internal wall of the test cavity is provided with a lower detecting component; the upper detecting component and the lower detecting component is arranged in a longitudinal symmetry form;

wherein the upper detecting component comprises a substrate, an electrode and a gas sensitive film bonded in sequence from top to bottom, and the substrate is bonded to the upper internal wall of the test cavity;

wherein a rubber airbag is disposed between the upper detecting component and the lower detecting component, and a friction film is bonded to the rubber airbag; an air inlet cylinder is connected to a left end of the rubber airbag, and an air outlet cylinder is connected to a right end of the rubber airbag; the air inlet cylinder extends out of the test cavity, and the air outlet cylinder is disposed in the test cavity;

wherein the rubber airbag is disposed in a longitudinal symmetry form, and a symmetric axis thereof coincides with a symmetric axis of the upper detecting component and the lower detecting component;

wherein the upper detecting component and the lower detecting component are both electrically connected to the digital electrometer, and the digital electrometer is grounded.

The beneficial effect/working principle of the technical solution is that the gas exhaled by the human body enters the rubber airbag through the air inlet cylinder, and the rubber airbag is squeezed and expanded by the gas. When the friction film bonded to the rubber airbag contacts the gas sensitive film and rubs, the friction film obtains electrons, so that the friction film and the gas sensitive film are charged with the same amount of electric charge. Since the distance difference between the friction film and the gas sensitive film with respect to the electrode is small, the sensing ability of the electrode is almost the same, so the electrode surface has no charge. When the human body inhales, the rubber bladder shrinks, and the friction film is separated from the gas sensitive film. Since the friction charge stays on the friction film and the gas sensitive film for a long time, although the friction film and the gas sensitive film are separated, the relative position of the gas sensitive film and the electrode is always unchanged under electrostatic induction, so the negative electric charge of the electrode induced by the gas sensitive film is unchanged. Meanwhile, when the friction film is away from the electrode, the electrostatic induction capability is decreased, and the positive electric charge of the electrode induced by the friction film changes with the distance change between the friction film and the electrode, so it is necessary to draw negative charge from the ground to form electrostatic shield, which generates an electric current. As the rubber airbag shrinks to the limit, the negative charge for electrostatic shielding extracted from the ground reaches a maximum value. When the human body exhales again, the rubber airbag re-expands. Because the friction film gets close to the electrode, the number of positive charges induced by the friction film begins to increase, so the negative charge requirement of the electrostatic shield is reduced, and the excess negative charge will flow back to the ground to form the opposite current. When the friction film is in contact with the gas sensitive film, the initial charge transfer process will be repeated. Periodic breath drives the rubber airbag to expand and shrink, which can provide periodic signal output without the need of external power supply system. Furthermore, the kinetic energy of the breathing gas can be directly used to drive the expansion of the rubber airbag, so as to achieve spontaneous detection of respiratory frequency and respiratory volume.

Preferably, the upper detecting component has an air inlet extending through the upper detecting component, and the air inlet is connected to an air inlet pipe, wherein the air inlet pipe extends through the testing cavity and protrudes;

the lower detecting component has an air outlet extending through the lower detecting component, and the air outlet is connected with an air outlet pipe, wherein the air outlet pipe extends through the testing cavity and protrudes.

The working principle/beneficial effect of the technical solution is that the digital electrometer performs simulation test data acquisition, and the response of the target gas concentration needs to be firstly calibrated before testing the concentration of the target gas in the exhaled gas. The rubber airbag is expanded or contracted, so that the gas in the test cavity forms a cycle. At the same time, air mixed with the target gas enters the test cavity from the air inlet pipe, and the gas is discharged through the air outlet pipe. After venting for a period of time, the source of the air intake should be disconnected and an air outlet valve should be closed to perform static detection.

The digital electrometer performs test data acquisition, and the breathing gas is introduced into the rubber airbag from the air inlet cylinder through a drying process and a current limiting process at a front end, wherein a flow restricting valve is adjusted according to a flow meter display, in such a manner that a flow rate is identical to that of calibration test. The air outlet cylinder passes the breathing gas into the test cavity. The output voltage/current signal driven by the breathing gas is compared with those driven to by the target gas of different concentrations to obtain the concentration of the target gas in the human breathing gas, which means the concentration of the target gas in the breathing gas is spontaneously detected.

Preferably, the rubber bag is a nitrile rubber bag.

Preferably, the electrode is made by depositing a layer of metal on a surface of an organic film.

Preferably, the metal is one of aluminum, nickel, copper, silver, and gold; the organic film is made of polyethylene terephthalate or polyimide.

Preferably, a thickness of the electrode is 100-200 nm.

Preferably, the gas sensitive film is made of a material selected from a group consisting of polyaniline, polyethylene oxide, polyethyleneimine, sodium polystyrene sultanate, polyaniline, polyimide, and graphene oxide.

Preferably, the friction film is made of nylon, polytetrafluoroethylene, polydimethylsiloxane, polyvinyl chloride, or polyimide.

Preferably, the friction film is made of the polytetrafluoroethylene.

The present invention also provides a preparation method of a breathing-driven flexible respiratory sensor, comprising steps of:

1) depositing an electrode on a substrate by thermal evaporation, and spraying a gas sensitive film on a surface of the electrode to obtain an upper detecting component, wherein a lower detecting component has an identical structure as the upper detecting component;

2) respectively bonding the upper detecting component and the lower detecting component obtained in the step 1) to an upper internal wall and a lower internal wall of a test cavity, and respectively bonding the substrates to the upper internal wall and the lower internal wall of the test cavity;

3) connecting two wires to the lower detection component and the upper detection component respectively, and electrically connecting the other ends of the two wires to a digital electrometer, and grounding the digital electrometer; and 4) respectively communicating an air outlet cylinder and an air inlet cylinder with a left end and a right end of a rubber airbag, wherein the air outlet cylinder is disposed in the test cavity and the air inlet cylinder extends out of the test cavity; the rubber airbag is installed at a center of the test cavity, and a center point of the rubber airbag coincides with a center point of the test cavity.

Element reference: 1—test cavity; 2—substrate; 3—electrode; 4—gas sensitive film; 5—air inlet pipe; 6—friction film; 7—rubber airbag; 8—air inlet cylinder; 9—air outlet cylinder; 10—digital electrometer; 11—air outlet pipe; 12—target gas; 13—dry air; 14—syringe; 15—stepper motor.

DETAILED DESCRIPTION OF THE PREFERRED EMBODIMENT

The present invention is based on combination of frictional electrification and electrostatic induction, and the difference in triboelectricity between the gas sensitive material and the opposite friction material causes the material to continuously Is accumulate/release charge during the process of contacting and separating, thereby generating alternating currents in the external circuit for spontaneously detecting respiratory frequency, respiratory volume, and target gas concentration in the breathing gas.

In order to make those skilled in the art understand the production process and technical effects of the present invention in detail, the specific embodiments of the present invention are described in detail below with reference to the technical proposal and drawings.

Embodiment 1

Figure 1:
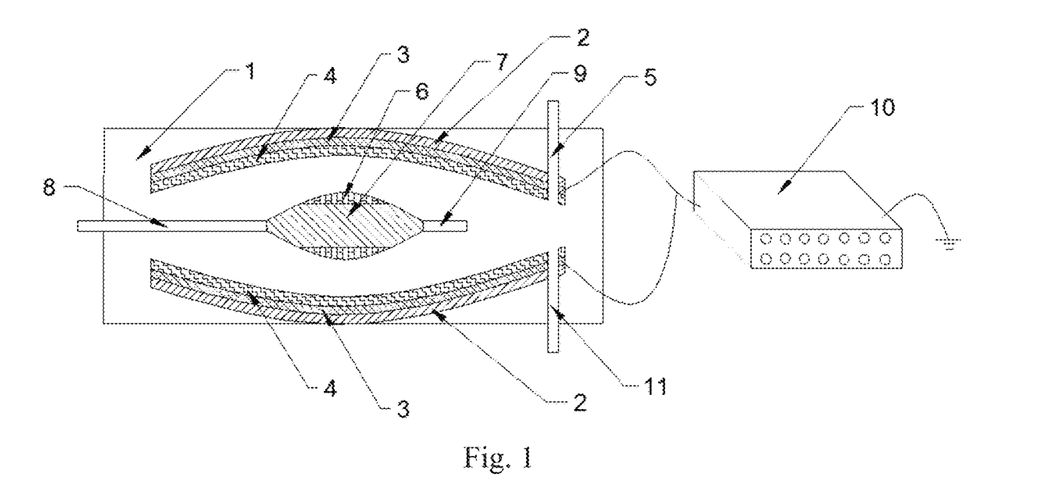
FIG. 1 is a structural view of the present invention.

Referring to FIG. 1, a basic structure of a breathing-driven flexible respiratory sensor is shown, comprising: a test cavity 1 and a digital electrometer 10, wherein an upper internal wall of the test cavity 1 is provided with an upper detecting component, and a lower internal wall of the test cavity 1 is provided with a lower detecting component; the upper detecting component and the lower detecting component is arranged in a longitudinal symmetry form; wherein the upper detecting component comprises a substrate 2, an electrode 3 and a gas sensitive film 4 (all reference number 4 in the embodiment 1 refers to the gas sensitive film) bonded in sequence from top to bottom, and the substrate 2 is bonded to the upper internal wall of the test cavity 1; wherein a rubber airbag 7 is disposed between the upper detecting component and the lower detecting component, and a friction film 6 is bonded to the rubber airbag 7; an air inlet cylinder 8 is connected to a left end of the rubber airbag 7, and an air outlet cylinder 9 is connected to a right end of the rubber airbag 7; the air inlet cylinder 8 extends out of the test cavity 1, and the air outlet cylinder 9 is disposed in the test cavity 1; wherein the rubber airbag 7 is disposed in a longitudinal symmetry form, and a symmetric axis thereof coincides with a symmetric axis of the upper detecting component and the lower detecting component; the upper detecting component and the lower detecting component are both electrically connected to the digital electrometer 10, and the digital electrometer 10 is grounded;

wherein the digital electrometer 10 is a Keithley 6514 digital electrometer, the friction film 6 is a polytetrafluoroethylene film, the electrode 3 is a gold electrode, the friction film 4 is a nylon film, and the rubber airbag 7 is a nitrile airbag.

A breathing-driven flexible respiratory sensor for monitoring human respiratory conditions (including respiratory frequency and respiratory volume) is provided, and preparation steps are as follows:

(1): taking a 2 mm-thick polymethyl methacrylate plexiglass plate and cutting into corresponding substrates by a laser cutter;

(2): washing a polyethylene terephthalate organic film having a thickness of 0.1 mm with a chemical reagent such as acetone, ethanol or the like, and drying;

(3): cutting the cleaned polyethylene terephthalate organic film into a 3 cm×3 cm square substrate by the laser cutter;

(4): depositing a layer of gold on a rectangular substrate by thermal evaporation to foci n two identical gold electrodes;

(5): transferring a layer of nylon film on surfaces of the gold electrodes, wherein a surface of the nylon film can be modified by laser treatment or the like;

(6): respectively attaching a side of the polyethylene terephthalate organic film with the gold electrode prepared in the step (5) to reserved areas of the upper substrate and the lower substrate cut in the step (1), wherein the nylon film is directed to an internal side of a test cavity; at the same time, wires are taken out from the two electrodes;

(7): taking a nitrile glove, cutting a middle finger of the glove into a 5 cm-long hollow cylinder, and then wrapping to seal both sides of the glove with an air inlet pipe and an air outlet pipe with sealant to form an airbag-like structure, and finally adhering a tetrafluoroethylene film on the airbag with a double-sided tape;

(8): assembling the cut polymethyl methacrylate plexiglass plate into a package cavity by using two-liquid mixed hardening glue, and then fixing a nitrile airbag fixing device in a middle of the cavity, wherein the nitrile airbag is on the same vertical line as the gold electrodes and the assembly is completed; and (9): using the Keithley 6514 digital electrometer for data acquisition, wherein after a front-end drying process, breathing gas enters the nitrile airbag from the air inlet pipe through a flow indicator, and the air outlet pipe passes the breathing gas into the test cavity; the respiratory rate is obtained by calculating the number of waveforms output per unit time, and respiratory volume is obtained by observing the peak value of the output waveform.

Figure 2:
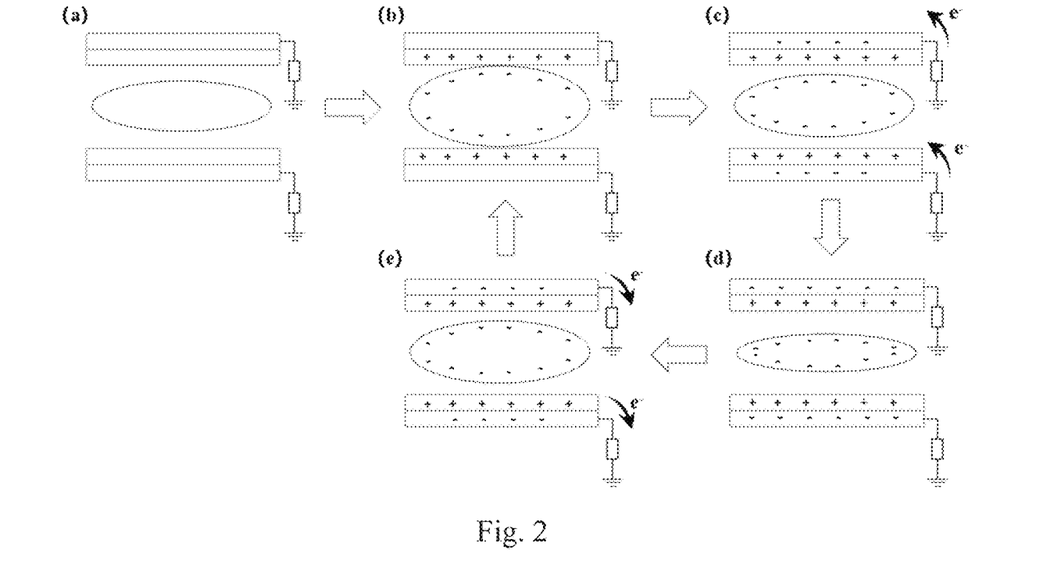
FIG. 2 illustrates a working process of a flexible respiratory sensor of an embodiment 1.

The power generation principle of the respiratory sensor based on the contact-separation type monitoring of human breathing is shown in FIG. 2. As shown in FIG. 2($a$), in the initial position, the system is in a state of no charge transfer due to the contact of the frictionless material. At this time, the gold electrode has the same potential as the ground. As shown in FIG. 2($b$), under the action of the gas, the nitrile airbag is expanded. At this time, the polytetrafluoroethylene attached to the surface of the nitrile airbag is in contact with the opposite nylon film. Because frictional electrode order difference to between the nylon and the attached polytetrafluoroethylene is relatively large, when the two are close to each other, the polytetrafluoroethylene film will obtain electrons from the nylon file, so that the two contact faces are charged with an equal amount of opposite electric charges. Since the distance between the polytetrafluoroethylene and the nylon film is small, the sensing ability to the gold electrode is the same, so the surface of the gold electrode is not charged. Polytetrafluoroethylene and nylon are used as polymer insulation materials, and their triboelectric charge will stay on the surface of the material for a long time. Once the nitrile airbag gradually shrinks away from the nylon film due to the inhalation, the relative position of the nylon electrode and the gold electrode is always constant under the action of electrostatic induction, so the gold electrode is not changed due to the negative charge induced by the nylon. As the polytetrafluoroethylene is far away from the gold electrode, the electrostatic induction capability decreases, so the number of positive charges induced by the polytetrafluoroethylene due to the increase in the distance of the polytetrafluoroethylene from the gold electrode decreases. Therefore, it is necessary to extract negative charge from the ground to form an electrostatic shield, thereby generating a current as shown in FIG. 2(c). As the nitrile airbag reaches the limit of shrinkage, the negative charge drawn from the ground for electrostatic shielding reaches a maximum, as shown in FIG. 2(d). When the nitrile airbag begins to re-expand, as the polytetrafluoroethylene begins to approach the gold electrode, the number of positive charges induced by the polytetrafluoroethylene on the gold electrode begins to increase, so the negative charge requirement of the electrostatic shield decreases. As a result, the excess negative charge will flow back to form a current opposite to that of FIG. 2(c), as shown in FIG. 2(e). The airbag continues to expand until the polytetrafluoroethylene is re-contacted with the nylon and returns to the operation state shown in FIG. 2(b). Periodic breath drives the rubber airbag to expand and shrink, which can provide periodic signal output without the need of external power supply system.

Figure 3:
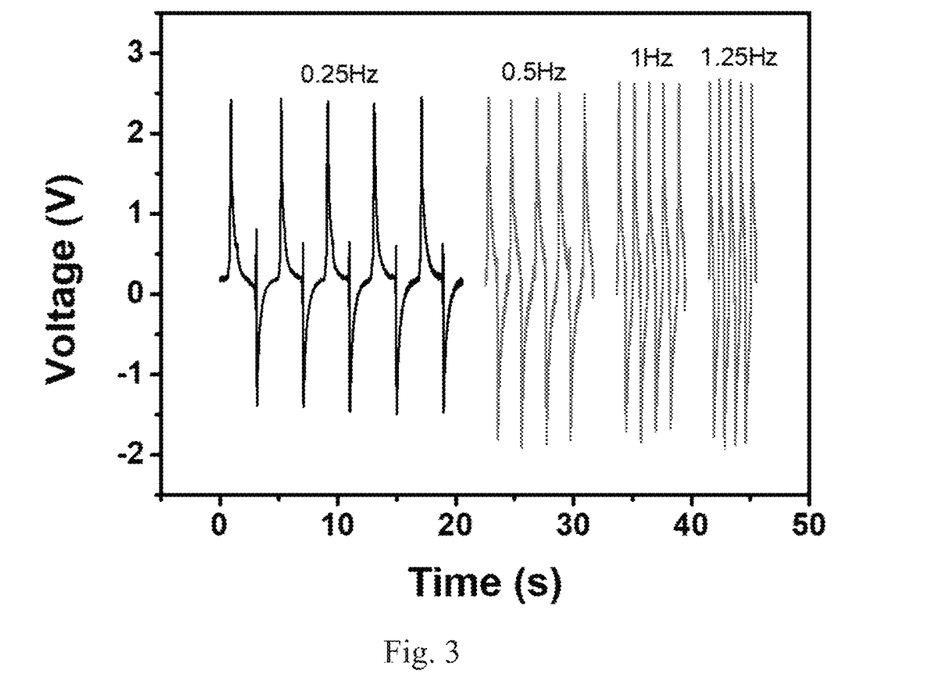
FIG. 3 illustrates a relationship between a gas flow frequency and a generator output under a constant breathing gas flow rate according to the embodiment 1.
Figure 4:
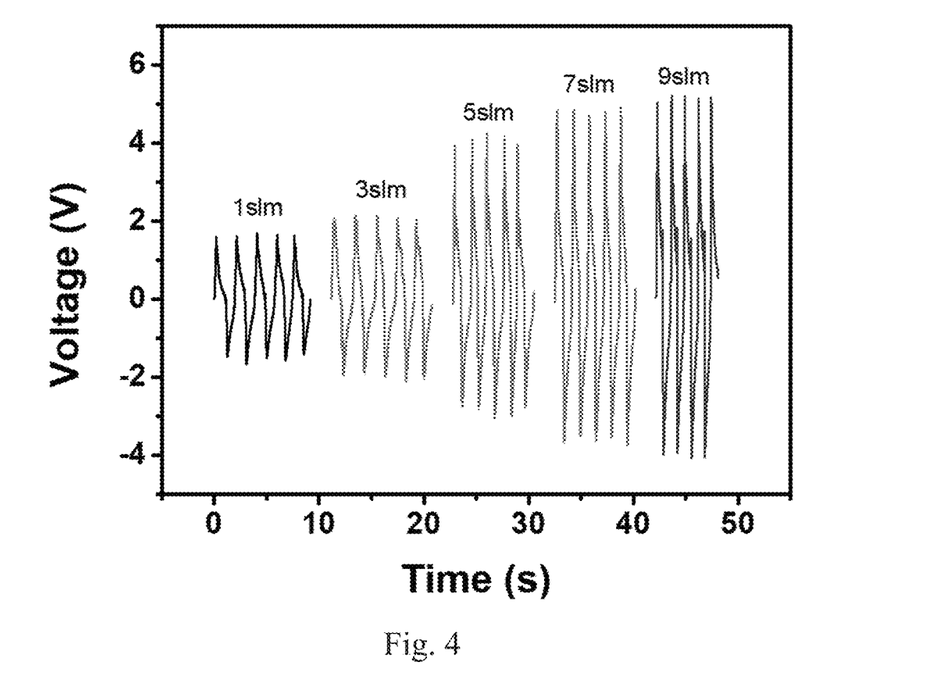
FIG. 4 illustrates a relationship between a gas flow rate and a generator output under a constant breathing gas flow frequency according to the embodiment 1.
Figure 5:
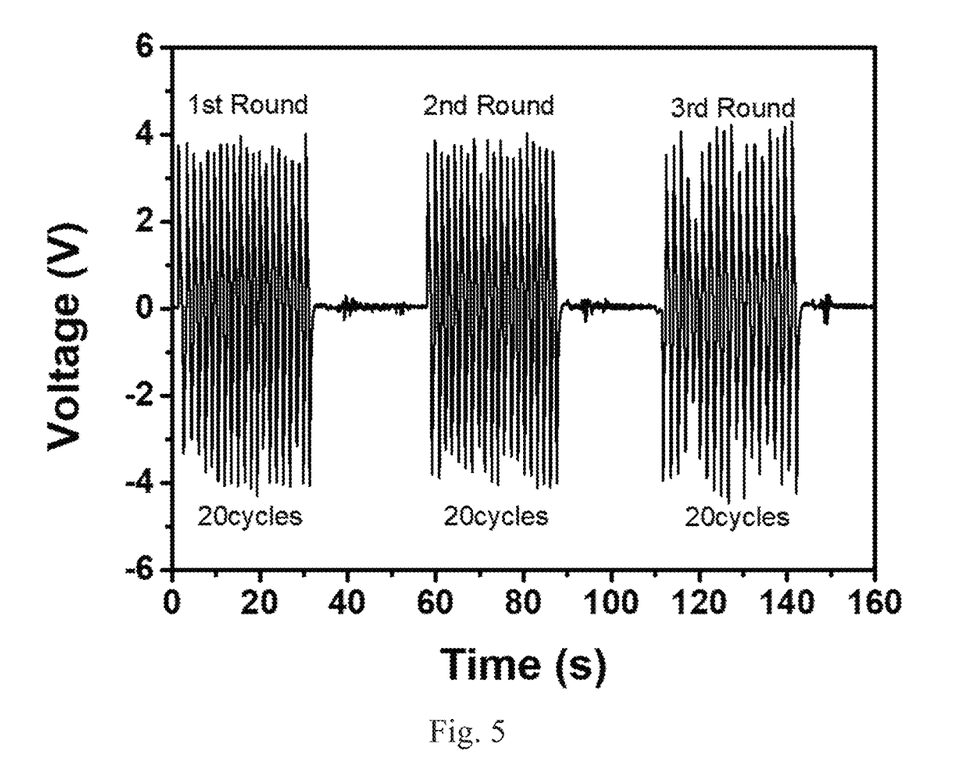
FIG. 5 illustrates a repeatability test under the constant breathing gas flow and frequency according to embodiment 1.

FIG. 3 is a relationship curve of respiratory frequency and output voltage under a constant respiratory flow rate (3.5 L/min). FIG. 4 is a relationship curve of respiratory flow and the output voltage under a constant respiratory rate (1 Hz). FIG. 5 shows stability and repeatability tests under constant respiratory flow and frequency (6 L/min, 0.66 Hz).

Embodiment 2

Figure 6:
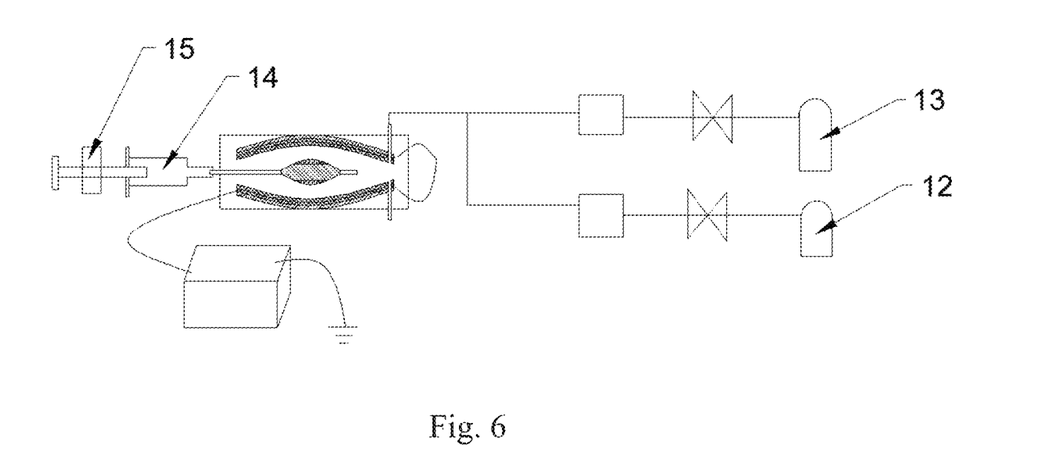
FIG. 6 illustrates a working process of a flexible respiratory sensor of an embodiment 2.

A breathing-driven flexible respiratory sensor for monitoring human respiratory conditions is provided, and preparation steps are as follows:

(1): taking a 2 mm-thick polymethyl methacrylate plexiglass plate and cutting into corresponding substrates by a laser cutter;

(2): washing a polyethylene terephthalate organic film having a thickness of 250 μm with a chemical reagent such as acetone, ethanol or the like, and drying;

(3): cutting the cleaned polyethylene terephthalate organic film into a 3 cm×3 cm square substrate by the laser cutter;

(4): depositing a layer of gold on a rectangular substrate by thermal evaporation to form two identical gold electrodes with a size of 3 cm×3 cm;

(5): assembling a polyaniline-metal oxide gas sensitive material by an in-situ polymerization method, and then attaching a layer of polyaniline gas sensitive film to the surface of gold electrodes by gas jet process;

(6): respectively attaching a side of the polyethylene terephthalate organic film with the gold electrode prepared in the step (5) to reserved areas of the upper substrate and the lower substrate cut in the step (1), wherein the polyaniline gas sensitive film is directed to an internal side of a test cavity; at the same time, wires are taken out from the two electrodes;

(7): preparing an intermediate layer device: taking a nitrile glove, cutting a middle finger of the glove into a 5 cm-long hollow cylinder, and then wrapping to seal both sides of the glove with an air inlet pipe and an air outlet pipe with sealant to form an airbag-like structure, and finally adhering a tetrafluoroethylene film on the airbag with a double-sided tape;

(8): assembling the cut polymethyl methacrylate plexiglass plate into a package cavity by using AB glue, and then fixing an intermediate layer device fixing device in a middle of the cavity, wherein the nitrile airbag is on the same vertical line as the gold electrodes, and the air inlet and outlet are respectively connected to the air pipes to complete the device assembly;

(9): using the Keithley 6514 digital electrometer for simulation test data acquisition; before testing the concentration of the target gas in the human exhaled breath, calibrating the response of different target gas concentrations; using a test system shown in FIG. 6, wherein a stepper motor 15 drives a syringe 14 to expand and contract the nitrile airbag and cause the gas in the test cavity to form a cycle; at the same time, the dry air 13 mixed with the target gas 12 enters the test cavity from the air inlet, and the gas is discharged through the air outlet; after venting for a period of time, the source of the air intake is disconnected and an air outlet valve is closed to perform static detection; and (10): using the Keithley 6514 digital electrometer for respiratory test data acquisition, wherein the human breathing gas is introduced into the rubber airbag from the air inlet cylinder through a drying process and a current limiting process at a front end, wherein a flow restricting valve is adjusted according to a flow meter display, in such a manner that a flow rate is identical to that of calibration test. The air outlet cylinder passes the breathing gas into the test cavity. The output voltage/current signal driven by the breathing gas is compared with those driven by the target gas of different concentrations to obtain the concentration of the target gas in the human breathing gas, which means the concentration of the target gas in the breathing gas is detected.

Figure 7:
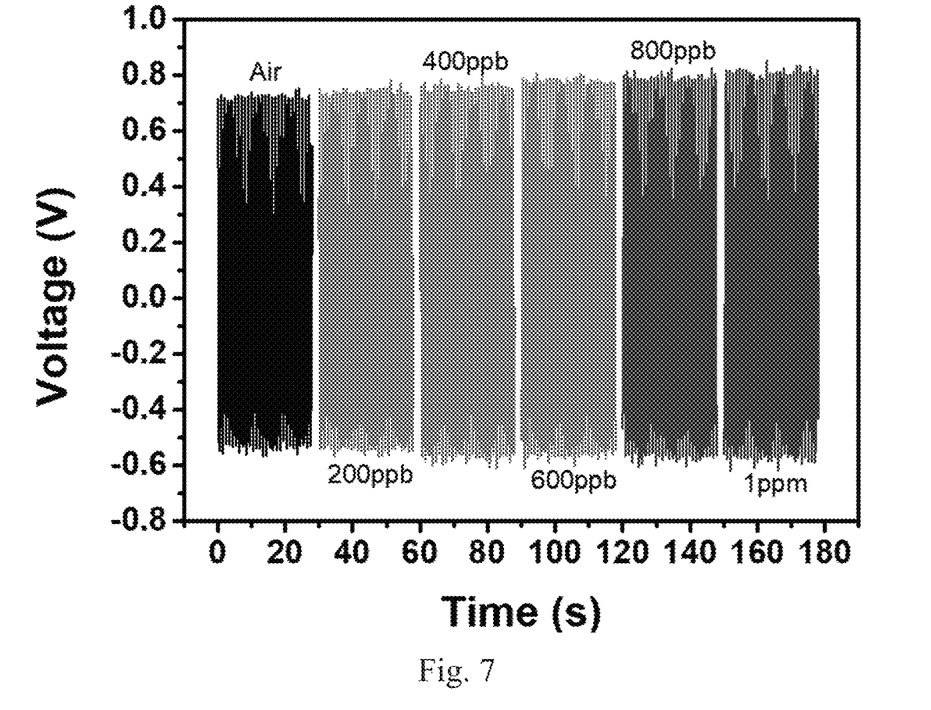
FIG. 7 illustrates a gas sensitive test under constant breathing gas flow rate and frequency according to embodiment 2.

FIG. 7 is a relationship curve of the target gas of different concentrations (here, ammonia gas) and the output open circuit voltage according to the simulation test (flow rate: 1.5 L/min, frequency: 0.5 Hz). It should be noted that in all the curves, the abscissa is time and the ordinate is voltage.

It should be noted that the above embodiments are only intended to illustrate and not to limit the technical solutions of the present invention. Although the present invention has been described in detail with reference to the embodiments thereof, those skilled in the art may make any modifications or partial substitutions within the spirit and scope of the present invention, which are intended to be included within the scope of the appended claims.

What is claimed is:

1. A breathing-driven flexible respiratory sensor, comprising: a test cavity and a digital electrometer, wherein an upper internal wall of the test cavity is provided with an upper detecting component, and a lower internal wall of the test cavity is provided with a lower detecting component; the upper detecting component and the lower detecting component is arranged in a longitudinal symmetry form;

wherein the upper detecting component comprises a substrate, an electrode and a gas sensitive film bonded in sequence from top to bottom, and the substrate is bonded to the upper internal wall of the test cavity;

wherein a rubber airbag is disposed between the upper detecting component and the lower detecting component, and a friction film is bonded to the rubber airbag; an air inlet cylinder is connected to a left end of the rubber airbag, and an air outlet cylinder is connected to a right end of the rubber airbag; the air inlet cylinder extends out of the test cavity, and the air outlet cylinder is disposed in the test cavity;

wherein the rubber airbag is disposed in a longitudinal symmetry form, and a symmetric axis thereof coincides with a symmetric axis of the upper detecting component and the lower detecting component; the upper detecting component and the lower detecting component are both electrically connected to the digital electrometer, and the digital electrometer is grounded;

wherein the upper detecting component has an air inlet extending through the upper detecting component, and the air inlet is connected to an air inlet pipe, wherein the air inlet pipe extends through the test cavity and protrudes;

the lower detecting component has an air outlet extending through the lower detecting component, and the air outlet is connected with an air outlet pipe, wherein the air outlet pipe extends through the test cavity and protrudes;

during testing, the rubber airbag is expanded or contracted, so that gas in the test cavity forms a cycle, the rubber airbag to which a friction material is attached undergoes expansion-contraction, causing contact-separation with the gas sensitive film, wherein induced charges on the electrode form a loop with the ground, thereby generating an alternating output, air mixed with a target gas enters the test cavity from the air inlet pipe, and the gas is discharged through the air outlet pipe.

2. The breathing-driven flexible respiratory sensor, as recited in claim 1, wherein the rubber airbag is a nitrile rubber airbag.

3. The breathing-driven flexible respiratory sensor, as recited in claim 1, wherein the electrode is made by depositing a layer of metal on a surface of an organic film.

4. The breathing-driven flexible respiratory sensor, as recited in claim 2, wherein the electrode is made by depositing a layer of metal on a surface of an organic film.

5. The breathing-driven flexible respiratory sensor, as recited in claim 3, wherein the metal is one of aluminum, nickel, copper, silver, and gold; the organic film is made of polyethylene terephthalate or polyimide.

6. The breathing-driven flexible respiratory sensor, as recited in claim 4, wherein the metal is one of aluminum, nickel, copper, silver, and gold; the organic film is made of polyethylene terephthalate or polyimide.

7. The breathing-driven flexible respiratory sensor, as recited in claim 1, wherein a thickness of the electrode is 100-200 nm.

8. The breathing-driven flexible respiratory sensor, as recited in claim 1, wherein the gas sensitive film is made of a material selected from a group consisting of polyaniline, polyethylene oxide, polyethyleneimine, sodium polystyrene sulfonate, polyaniline, polyimide, and graphene oxide.

9. The breathing-driven flexible respiratory sensor, as recited in claim 1, wherein the friction film is made of nylon, polytetrafluoroethylene, polydimethylsiloxane, polyvinyl chloride, or polyimide.

10. The breathing-driven flexible respiratory sensor, as recited in claim 1, wherein triboelectric properties of the gas sensitive film and the friction film are opposite.

11. The breathing-driven flexible respiratory sensor, as recited in claim 9, wherein the friction film is made of the polytetrafluoroethylene.

* * * * *